United States Patent
Kimata et al.

(10) Patent No.: US 7,643,737 B2
(45) Date of Patent: Jan. 5, 2010

(54) LINE OF SIGHT DETECTION APPARATUS

(75) Inventors: Akihito Kimata, Utsunomiya (JP); Akio Takahashi, Shioya-gun (JP)

(73) Assignee: Honda Motor Co., Ltd., Tokyo (JP)

( * ) Notice: Subject to any disclaimer, the term of this patent is extended or adjusted under 35 U.S.C. 154(b) by 329 days.

(21) Appl. No.: 11/689,145

(22) Filed: Mar. 21, 2007

(65) Prior Publication Data
US 2007/0222947 A1    Sep. 27, 2007

(30) Foreign Application Priority Data
Mar. 27, 2006   (JP) .............................. 2006-085905

(51) Int. Cl.
*G03B 17/00*   (2006.01)
*G03B 17/48*   (2006.01)

(52) U.S. Cl. ........................................ 396/51; 396/429

(58) Field of Classification Search .................... 396/51, 396/429; 348/77, 78, 169; 351/208, 209, 351/210
See application file for complete search history.

(56) References Cited

U.S. PATENT DOCUMENTS

| 7,231,051 | B2 | 6/2007 | Paviot et al. |
| 2004/0070729 | A1 | 4/2004 | Wiebe et al. |
| 2005/0225723 | A1* | 10/2005 | Pilu ........................... 351/209 |
| 2007/0066916 | A1* | 3/2007 | Lemos ........................ 600/558 |

FOREIGN PATENT DOCUMENTS

| DE | 100 39 795 | 3/2002 |
| DE | 102 17 822 | 9/2003 |
| EP | 1 405 157 | 4/2004 |
| JP | 08-297019 | 11/1996 |

\* cited by examiner

*Primary Examiner*—Rodney E Fuller
(74) *Attorney, Agent, or Firm*—Rankin, Hill & Clark LLP

(57) ABSTRACT

A line of sight detection apparatus includes: a line of sight detection device which detects the line of sight of an occupant; an operation detection device which detects the operation of on-board equipment by the occupant; and a calibration device which calibrates a detection value of the line of sight detection device based on the operation of the on-board equipment by the occupant which is detected by the operation detection device and position data of the on-board equipment.

1 Claim, 3 Drawing Sheets

LINE OF SIGHT DETECTION APPARATUS

BACKGROUND OF THE INVENTION

1. Field of the Invention

This invention is related to a line of sight detection apparatus.

Priority is claimed on Japanese Patent Application No. 2006-085905, filed Mar. 27, 2006, the contents of which are incorporated herein by reference.

2. Description of Related Art

Conventionally, an apparatus which detects the line of sight of a vehicle driver based on, for example, a retinal reflection image, a corneal reaction image, and a pictorial image of the face of the vehicle driver is known (e.g., refer to Japanese Unexamined Patent Application, First Publication No. H08-297019).

In the abovementioned apparatus according to one example of the prior art, some calibration methods to calibrate the detected line of sight are known. For example, the calibration is operated by detecting the line of sight in a state of a driver gazes at a predetermined designated position, or by using calibration value which is statistically calculated beforehand from a plurality of physiques.

However, particular input operations or movements of the line of sight only for calibration are necessary for each new driver in order to calibrate a line of sight detection apparatus by the driver's gazing at the designated position. Therefore, when a plurality of drivers alternate, complicated procedures would be required since the calibration operation is needed for each alternation.

Furthermore, errors which occur in every driver cannot be reduced when calibrating by the calibration value which is statistically calculated.

SUMMARY OF THE INVENTION

The present invention has been realized in view of the above-described situation and has an object to provide a line of sight detection apparatus which can easily calibrate the detection of the line of sight of an operator.

In order to solve the problem and achieve the object, a line of sight detection apparatus of the present invention includes: a line of sight detection device which detects the line of sight of an occupant; an operation detection device which detects the operation of on-board equipment by the occupant; and a calibration device which calibrates the detection value of the line of sight detection device based on the operation of the on-board equipment by the occupant which is detected by the operation detection device and position data of the on-board equipment.

According to the above line of sight detection apparatus, for example, particular operations of the driver for calibrating the line of sight detection device are not required, and precise calibration can be operated in accordance with the series of driving operations by the driver easily and efficiently. Therefore, the driver can be prevented from being distracted by the calibration.

In addition, according to the line of sight detection apparatus of the present invention, the calibration device can inhibit calibration of the detection value when the difference between the position data of the on-board equipment which is a object of operation by the occupant and which is detected by the operation detection device and sight position data in accordance with the detection value from the line of sight detection device being larger than a predetermined value.

According to the above line of sight detection apparatus, the reliability of the calibration can be improved.

As explained above, according to the line of sight detection apparatus of the present invention, the precise calibration can be operated in accordance with the series of driving operations by the driver easily and efficiently. Therefore, the driver can be prevented from being distracted by the calibration.

In addition, according to the line of sight detection apparatus of the present invention, the reliability of the calibration can be improved.

DETAILED DESCRIPTION OF THE INVENTION

Below, a line of sight detection apparatus according to one embodiment of the present invention will be explained referring to the attached drawings.

Figure 1:
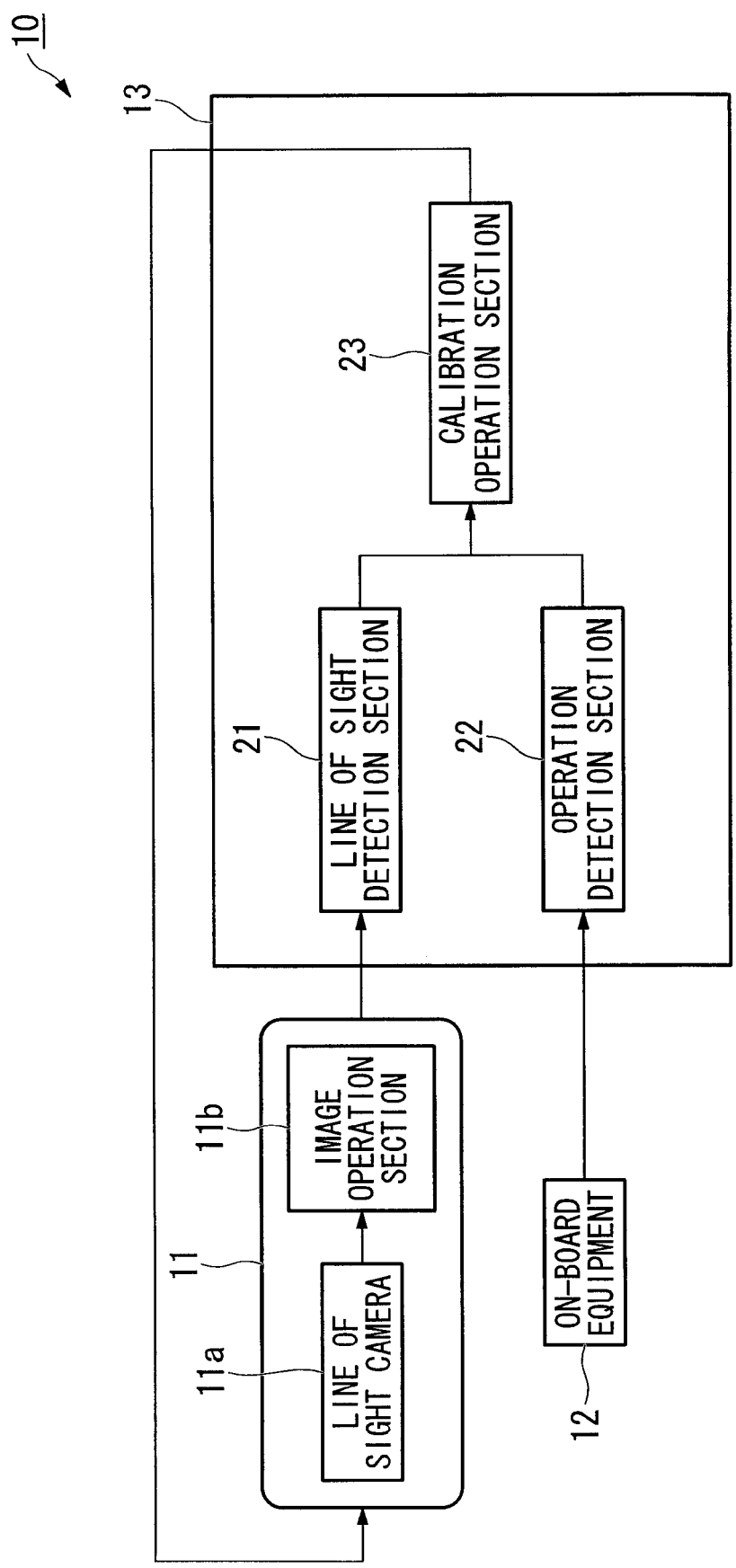
FIG. 1 is a schematic view showing a line of sight detection apparatus according to an embodiment of the present invention.

A line of sight detection apparatus 10 of the present embodiment is, as shown in FIG. 1 for example, constituted from an eyeball sensor 11, an on-board equipment 12, and a control device 13.

Figure 2:
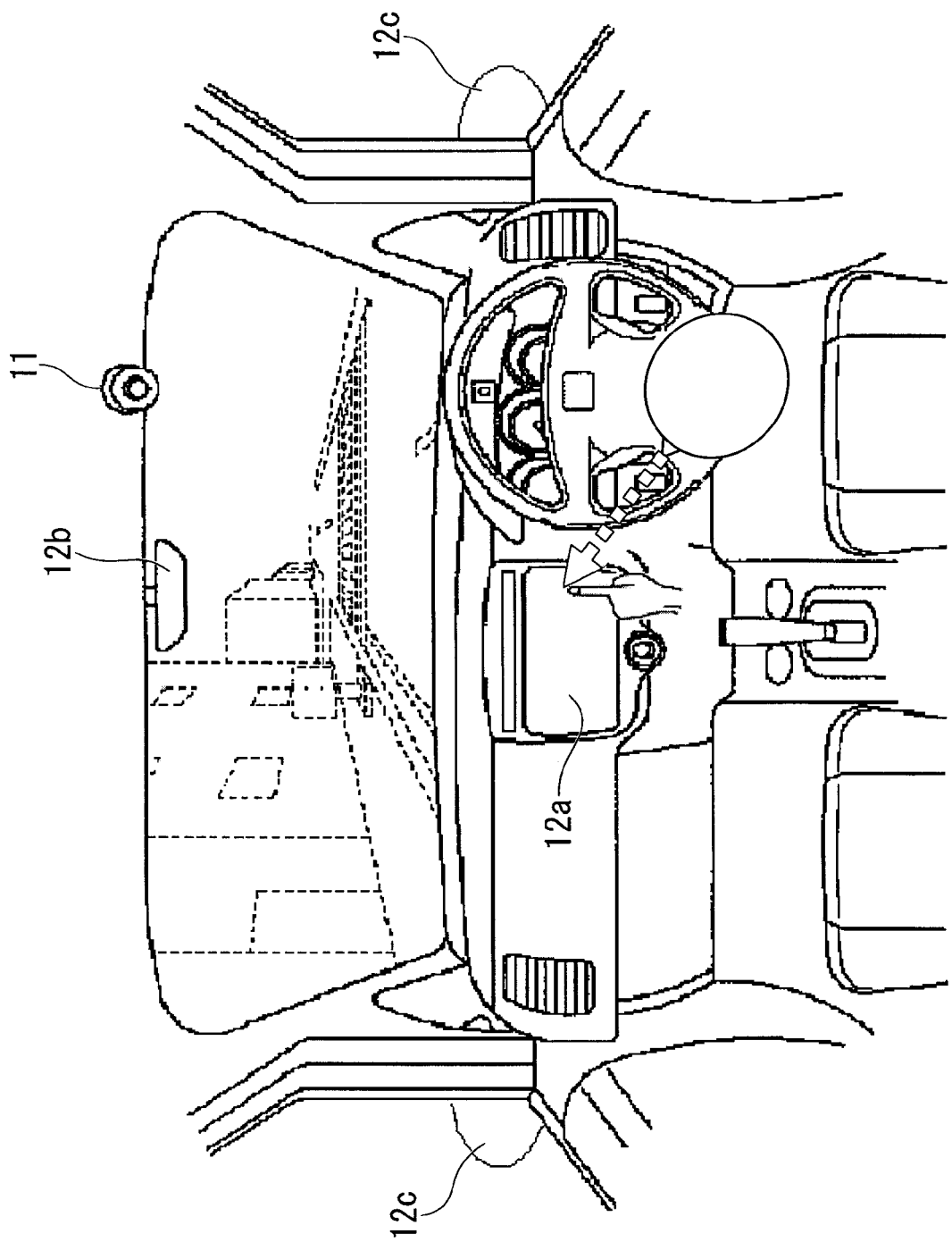
FIG. 2 is a view showing an example of the on-board equipment shown in FIG. 1.

The eyeball sensor 11 is, as shown in FIG. 2 for example, equipped at a position proximal to a rear view mirror in a compartment toward the driver's side or the like, that is, a position at least where an image of the eyeball of the driver is capturable. The eyeball sensor 11 is constituted from, for example, an eyeball camera (line of sight camera) 11a including a CCD camera, a CMOS camera or the like capturable in a visible light radiation area and an infrared radiation and an eyeball image operation section 11b.

The eyeball camera 11a captures a visible light radiation reflected from the face or the eyeball of the occupant when capturable in the visible light radiation area, or when capturable in the infrared radiation area, captures a reflection of infrared radiation radiated to the eyeball of the driver from an appropriate floodlight (not illustrated).

The eyeball image operation section 11b generates image data having two-dimensional arrayed picture elements by predetermined image processing such as filtering, binarize processing or the like with regard to a visible light radiation image or an infrared radiation image obtained from the capturing of the eyeball camera 11a. The image data is outputted to the control device 13.

The on-board equipment 12 are devices of which the possibility of the line of sight of the driver is set at a predetermined position is relatively high when the driver operates, such as a navigation equipment 12a, a rear view mirror 12b, motor-driven side mirrors 12c, and the like shown in FIG. 2.

The control device 13 is constituted from, for example, a line of sight detection section 21, an operation detection section 22, and a calibration operation section 23.

The line of sight detection section 21 operates predetermined recognitions of the face or the eyeball of the driver as detection subjects with respect to image data input from the eyeball sensor 11. Next, the line of sight detection section 21 detects the position of the eyeball of the driver, a line of sight vector (a line of sight direction) of the driver, and a target position of the line of sight (a sight position data) based on the recognition result.

The operation detection section 22 detects the existence of an operation by the driver with regard to the on-board equipment 12 and the content of operation.

The calibration operation section 23 calibrates the detection value of the eyeball sensor 11 based on the line of sight vector (line of sight direction) of the driver and the target position of the line of sight detected by the line of sight detection section 21 and the detection result of the operation detection section 22.

For example, the calibration operation section 23 obtains the detection result of the operation detection section 22, that is to say, a predetermined position data previously set corresponding to the operation content in accordance with the existence of the operation and the operation content of the driver to the on-board equipment 12 (i.e., the position of the operating parts provided with the navigation equipment 12*a* such as operating button or the like, or the positions of the rear view mirror 12*b* or the motor-driven side mirror 12*c* shown in FIG. 2). Then, the calibration operation section 23 decides whether or not the difference between the obtained position data and the sight position data (e.g., the target position of the line of sight) detected by the line of sight detection section 21 at the timing of detection of input to the on-board equipments 12 by the driver is less than a predetermined value. In addition, the difference between the line of sight vector (the line of sight direction) f(a) detected by the line of sight detection section 21 and a predetermined direction G previously set corresponding to the operation contents may be decided whether or not it is less than a predetermined value β.

Then, if the decision result is "YES", the detection value of the eyeball sensor 11 is calibrated corresponding to the difference.

On the other hand, if the decision result is "NO", the line of sight direction of the driver is decided to be independent of the driver's operation with regard to the on-board equipment 12 and the calibration is inhibited from executing.

A predetermined parameter "a" (e.g., a radius of the eyeball) with regard to the line of sight direction f(a), which is the detection result of the line of sight detection section 21, is corrected based on formula (1) below when the difference (|G−f(a)|) between the line of sight direction f(a) and the predetermined direction G is not more than the predetermined value β. In the formula (1) below, a corrected parameter $a_{(k+1)}$ is calculated based on an appropriate coefficient "α", any natural number "k", and an uncorrected parameter $a_{(k)}=a$

[Formula (1)]

$$a_{(k+1)} = a_{(k)} + \alpha \cdot (G - f(a)) \cdot \left.\frac{\partial (f(a))}{\partial a}\right|_{a=a_{(k)}} \quad (1)$$

For example, when the navigation equipment 12*a* shown in FIG. 2 is set as the on-board equipment 12, firstly, output signals from the various operating buttons or the like of the navigation equipment 12*a* which detects the operating input of the driver are detected by the operation detection section 22. Secondly, the calibration operation section 23 obtains the prescribed position data previously set in accordance with the detection result of the operation detection section 22. Precise calibration is possible when the navigation equipment 12*a* is operated since the possibility of the driver gazing in the prescribed position or the like on a display screen of the navigation equipment 12*a* is relatively high.

For example, when the motor-driven side mirror 12*c* shown in FIG. 2 is set as the on-board equipment 12, output signals from the various operating buttons or the like of the motor-driven side mirror 12*c* which detects the operating input of the driver are detected by the operation detection section 22. Secondly, the calibration operation section 23 obtains the prescribed position data previously set in accordance with the detection result of the operation detection section 22. Precise calibration is possible since the possibility that the driver does not gaze at the side mirrors when adjusting the angle of the left and right side mirrors is very low, and further, data at two points with regard to the each of the left and right side mirrors which are appreciably differ in relative coordinate position thereof are used.

For example, when the rear view mirror 12*b* shown in FIG. 2 is set as the on-board equipment 12, detection signal from an appropriate sensor (not illustrated) which is provided with the rear view mirror 12*b* and which detects the operation of the driver (e.g., contacts to the rear view mirror 12*b* of the driver, displacements of the rear view mirror 12*b*, or the like) is detected by the operation detection section 22. Secondly, the calibration operation section 23 obtains the prescribed position data previously set in accordance with the detection result of the operation detection section 22. Precise calibration is possible since the possibility that the driver does not gaze at the rear view mirror 12*b* when adjusting the angle of the rear view mirror 12*b* is very low.

The line of sight detection apparatus 10 of the present embodiment is provided with the abovementioned constitution. Next, an act of the line of sight detection apparatus 10 will be explained.

Figure 3:
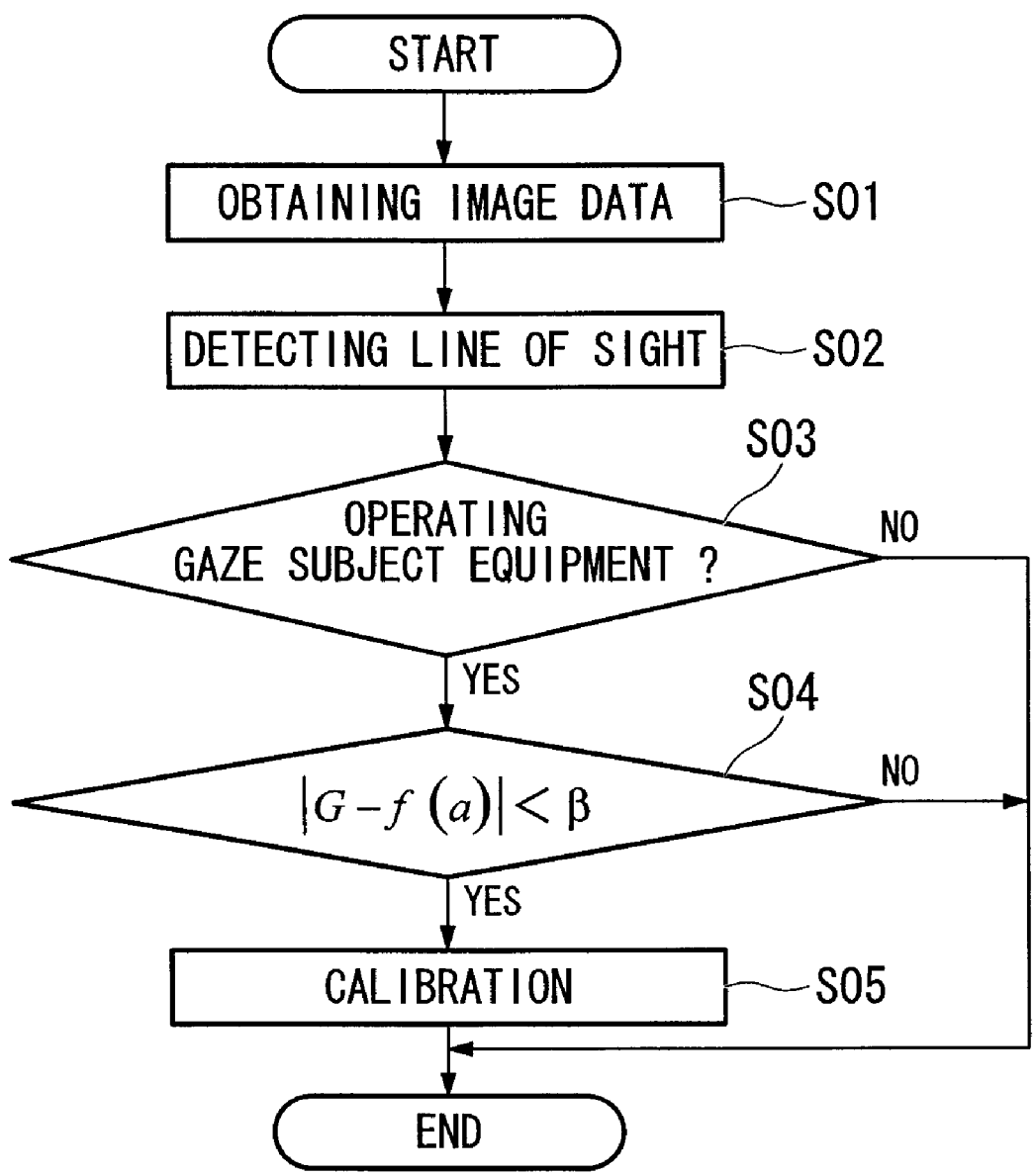
FIG. 3 is a flow diagram showing an operation of the line of sight detection apparatus according to the embodiment of the present invention.

First, image data output from the eyeball sensor 11 is obtained in Step S01 shown in FIG. 3.

Next, the line of sight is detected based on the obtained image data in Step S02.

Next, in Step S03, it is decided whether or not the driver operates the prescribed equipment which is gazed by the driver (e.g., the navigation equipment 12*a*, the rear view mirror 12*b*, the motor-driven side mirror 12*c*, and the like), that is to say, whether or not the driver operates the prescribed equipment which includes a predetermined portion having relatively high probability of being gazed by the driver while being operated by the driver.

If the decision result is "NO", the series of the processes is ended.

Otherwise, the decision result is "YES", and the process is advanced to Step S04.

In Step S04, it is decided whether or not the difference between the line of sight vector (the line of sight direction) f(a) detected by the line of sight detection section 21 and the predetermined direction G previously set corresponding to the operation contents is less than the predetermined value β.

If the decision result is "NO", the series of the process is ended.

Otherwise, the decision result is "YES", and the process is advanced to Step S05.

In Step S05, the detection result of the line of sight detection section 21 (e.g., the line of sight direction f(a)) is calibrated based on the above formula (1) in accordance with the difference (|G−f(a)|) between the line of sight vector (the line of sight direction) f(a) and the predetermined direction G previously set corresponding to the contents of the operation contents, and then the series of the process is ended.

As described above, according to the line of sight detection apparatus 10 of the present embodiment, precise calibration can be operated in accordance with the series of the driving operation by the driver easily and efficiently. Therefore, the driver can be prevented from being distracted by the calibration. Furthermore, the reliability of the calibration can be improved.

While a preferred embodiment of the invention has been described and illustrated above, it should be understood that this is an exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A line of sight detection apparatus comprising:
a line of sight detection device which detects the line of sight of an occupant;
an operation detection device which detects the operation of on-board equipment by the occupant; and
a calibration device which calibrates a detection value of the line of sight detection device based on the operation of the on-board equipment by the occupant which is detected by the operation detection device and position data of the on-board equipment, wherein
the calibration device inhibits calibration of the detection value when the difference between the position data of the on-board equipment which is an object of operation by the occupant and which is detected by the operation detection device and sight position data in accordance with the detection value from the line of sight detection device is larger than a predetermined value.

* * * * *